United States Patent

Curry

Patent Number: 5,480,615
Date of Patent: Jan. 2, 1996

[54] GERMICIDE DIFFUSER

[76] Inventor: Jeanette Curry, 945 E. 27th St., Paterson, N.J. 07513

[21] Appl. No.: 354,375

[22] Filed: Dec. 12, 1994

[51] Int. Cl.$^6$ ............................................. A61L 9/03
[52] U.S. Cl. ........................... 422/124; 422/125; 261/30; 261/91; 261/142
[58] Field of Search ................... 422/4, 120, 123, 422/124, 125; 239/159, 214.25, 220, 308, 310; 261/91, 142, 30, 76

[56] References Cited

U.S. PATENT DOCUMENTS

| | | | |
|---|---|---|---|
| 2,399,862 | 5/1946 | Feldermann | 261/30 |
| 2,472,011 | 5/1949 | Graham | 422/125 |
| 2,523,373 | 9/1950 | Jennings et al. | 422/125 |
| 2,554,868 | 5/1951 | Mills | 261/30 |
| 2,889,995 | 6/1959 | Borell | 239/310 |
| 2,937,419 | 5/1960 | Vaughn | 422/125 |
| 3,365,862 | 1/1968 | Flury | 261/30 |
| 3,605,385 | 9/1971 | Stoop | 261/30 |
| 3,674,421 | 7/1972 | Decupper | 422/121 |
| 3,873,806 | 3/1975 | Schossow | 422/125 |
| 4,882,096 | 11/1989 | Rueben | 261/30 |
| 4,931,654 | 6/1990 | Horng | 422/24 |
| 5,136,461 | 8/1992 | Zellweger | 422/121 |
| 5,141,722 | 8/1992 | Nagashima | 422/292 |
| 5,255,167 | 7/1993 | Wetzel | 422/121 |

*Primary Examiner*—Robert J. Warden
*Assistant Examiner*—Theresa T. Snider

[57] ABSTRACT

A diffuser for vaporizing and dispensing a fluid germicide to disinfect a room and associated equipment. The inventive device includes a vapor generating assembly for mechanically atomizing a fluid germicide. A blower assembly dilutes and heats the vapor and forces the same through a rectangular diffuser to coat the associated room and equipment with a fine mist of the germicide.

5 Claims, 3 Drawing Sheets

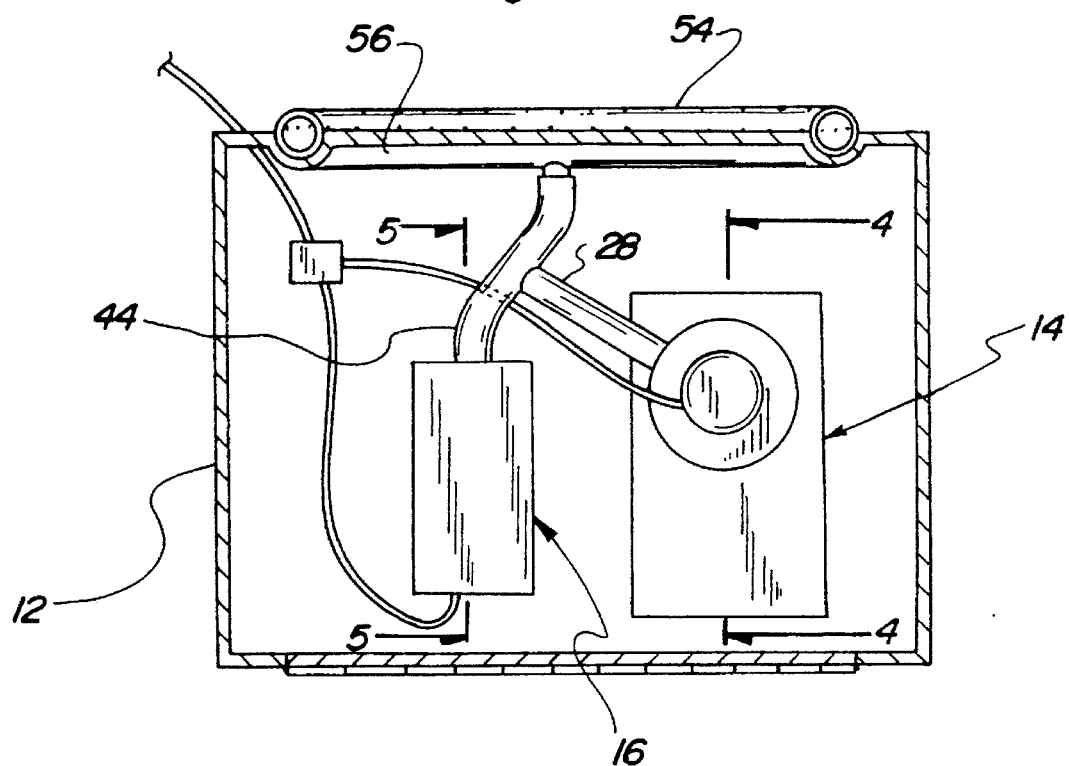
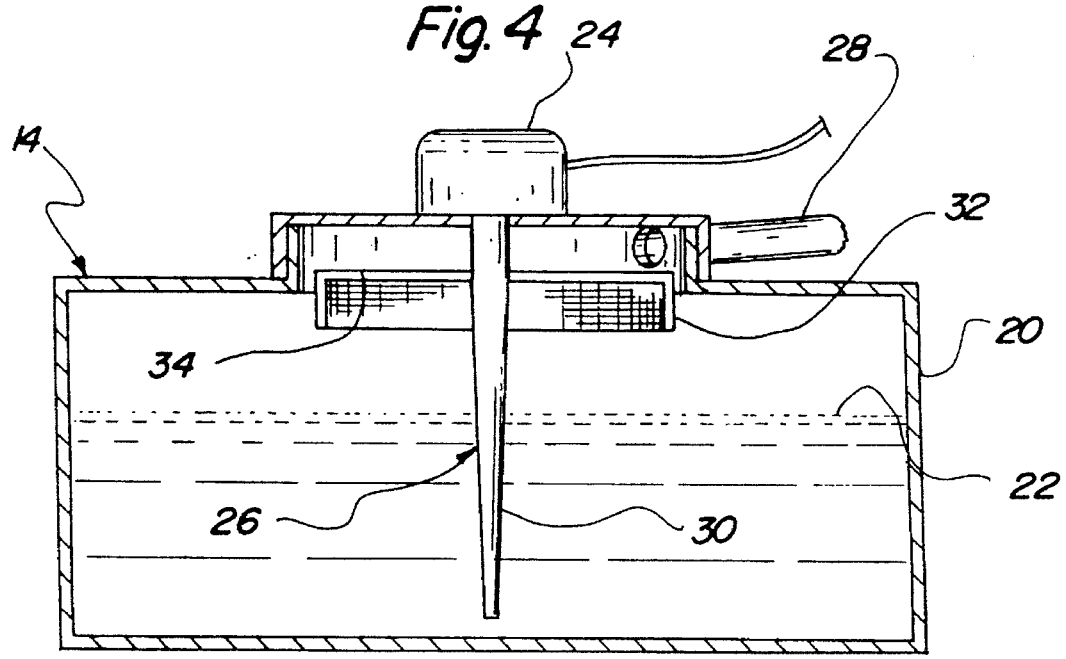

GERMICIDE DIFFUSER

BACKGROUND OF THE INVENTION

1. Field of the Invention

The present invention relates to spraying fluid distributors and more particularly pertains to a germicide diffuser for vaporizing and dispensing a fluid germicide to disinfect a room and associated equipment.

2. Description of the Prior Art

The use of spraying fluid distributors is known in the prior art. More specifically, spraying fluid distributors heretofore devised and utilized are known to consist basically of familiar, expected and obvious structural configurations, notwithstanding the myriad of designs encompassed by the crowded prior art which have been developed for the fulfillment of countless objectives and requirements.

Known prior art spraying fluid distributors include U.S. Pat. Nos. 3,674,421; 4,931,654; 5,136,461; 5,141,722; and U.S. Pat. No. 5,225,167.

While these devices fulfill their respective, particular objectives and requirements, the aforementioned patents do not disclose a germicide diffuser for vaporizing and dispensing a fluid germicide which includes a vapor generating assembly for mechanically atomizing a fluid germicide, and a blower assembly for diluting and heating the vapor and to force the vapor through a rectangular diffuser.

In these respects, the germicide diffuser according to the present invention substantially departs from the conventional concepts and designs of the prior art, and in so doing provides an apparatus primarily developed for the purpose of vaporizing and dispensing a fluid germicide to disinfect a room and associated equipment.

SUMMARY OF THE INVENTION

In view of the foregoing disadvantages inherent in the known types of spraying fluid distributors now present in the prior art, the present invention provides a new germicide diffuser construction wherein the same can be utilized for vaporizing and dispensing a fluid germicide. As such, the general purpose of the present invention, which will be described subsequently in greater detail, is to provide a new germicide diffuser apparatus and method which has many of the advantages of the spraying fluid distributors mentioned heretofore and many novel features that result in a germicide diffuser which is not anticipated, rendered obvious, suggested, or even implied by any of the prior art spraying fluid distributors, either alone or in any combination thereof.

To attain this, the present invention generally comprises a diffuser for vaporizing and dispensing a fluid germicide to disinfect a room and associated equipment. The inventive device includes a vapor generating assembly for mechanically atomizing a fluid germicide. A blower assembly dilutes and heats the vapor and forces the same through a rectangular diffuser to coat the associated room and equipment with a fine mist of the germicide.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new germicide diffuser apparatus and method which has many of the advantages of the spraying fluid distributors mentioned heretofore and many novel features that result in a germicide diffuser which is not anticipated, rendered obvious, suggested, or even implied by any of the prior art spraying fluid distributors, either alone or in any combination thereof.

It is another object of the present invention to provide a new germicide diffuser which may be easily and efficiently manufactured and marketed.

It is a further object of the present invention to provide a new germicide diffuser which is of a durable and reliable construction.

An even further object of the present invention is to provide a new germicide diffuser which is susceptible of a low cost of manufacture with regard to both materials and labor, and which accordingly is then susceptible of low prices of sale to the consuming public, thereby making such germicide diffusers economically available to the buying public.

Still yet another object of the present invention is to provide a new germicide diffuser which provides in the apparatuses and methods of the prior art some of the advantages thereof, while simultaneously overcoming some of the disadvantages normally associated therewith.

Still another object of the present invention is to provide a new germicide diffuser for vaporizing and dispensing a fluid germicide to disinfect a room and associated equipment.

Yet another object of the present invention is to provide a new germicide diffuser which includes a vapor generating assembly for mechanically atomizing a fluid germicide, and a blower assembly for diluting and heating the vapor and to force the vapor through a rectangular diffuser.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a cross sectional view taken along line 3—3. of FIG. 1.

FIG. 4 is a further cross sectional view taken along line 4—4 of FIG. 3.

DESCRIPTION OF THE PREFERRED EMBODIMENT

Figure 1:
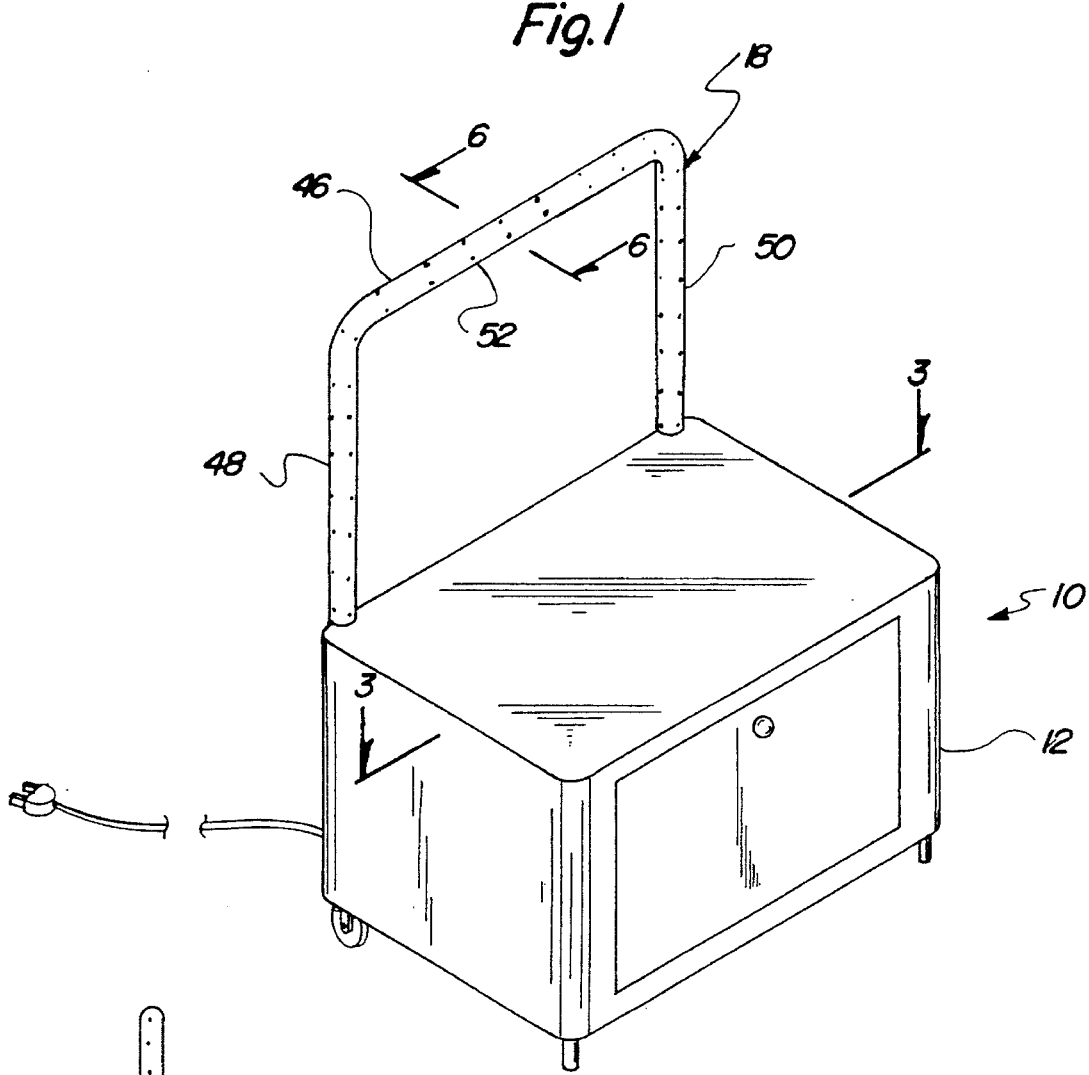
FIG. 1 is an isometric illustration of a germicide diffuser according to the present invention.
Figure 2:
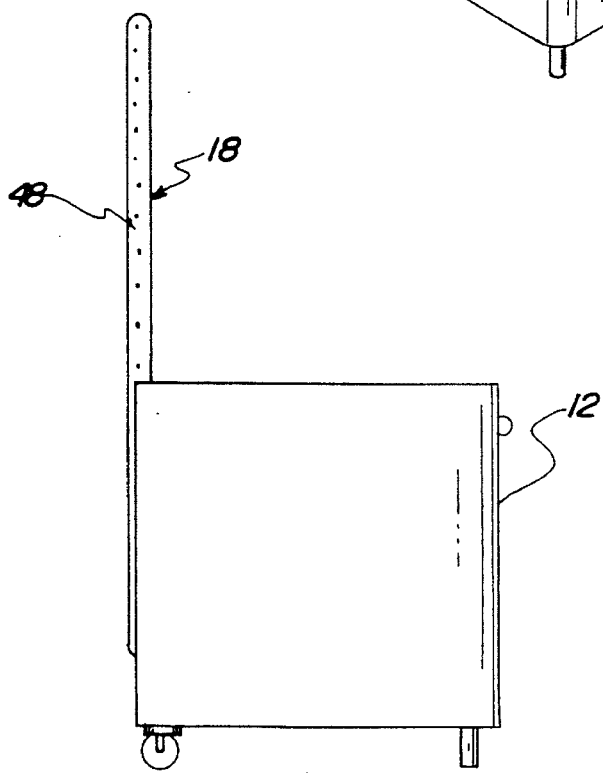
FIG. 2 is a side elevation view thereof.

With reference now to the drawings, and in particular to FIGS. 1–6 thereof, a new germicide diffuser embodying the principles and concepts of the present invention and generally designated by the reference numeral 10 will be described.

More specifically, it will be noted that the germicide diffuser 10 comprises a substantially rectangular housing 12 positionable within a room to be disinfected. As shown in FIG. 3, a vapor generating means 14 is mounted within the housing 12 for mechanically atomizing a fluid germicide. A blower means 16, also located within the housing 12, is in fluid communication with the vapor generating means 14 for diluting and heating a fluid vapor generated by the vapor generating means. A diffuser means 18 is mounted to an exterior of the housing 12 and fluidly communicates with the blower means 16 for distributing the diluted and heated vapor into the associated room.

As best illustrated in FIG. 4, it can be shown that the vapor generating means 14 according to the present invention 10 preferably comprises a fluid reservoir 20 within which a germicidal fluid 22 is positioned. A motor 24 is mounted to a top end of the fluid reservoir 20 and operates to rotate a centrifugal atomizer 26 coupled to the motor and extending into the fluid germicide 22. A vapor conduit 28 extends from an upper extent of the fluid reservoir 20 to a remote location to thus permit exiting of the atomized fluid germicide 22. Preferably, the centrifugal atomizer 26 comprises an elongated and tapered rotor 30 coupled to the motor shaft and extending into the fluid germicide 22. A cylindrical screen 32 is supported in a concentric orientation relative to the tapered rotor 30 by a connecting web 34 extending therebetween. By this structure, a rotation of the tapered rotor 30 will result in the fluid germicide 22 being drawn up the tapered rotor, whereby such fluid will be centrifugally forced from the rotor and caused to impact the cylindrical screen 32. Such impacting of the fluid germicide 22 against the rotating cylindrical screen 32 will mechanically atomize the fluid germicide to generate a vapor of the same. Such vapor is then expelled through a vapor conduit 28.

Figure 5:
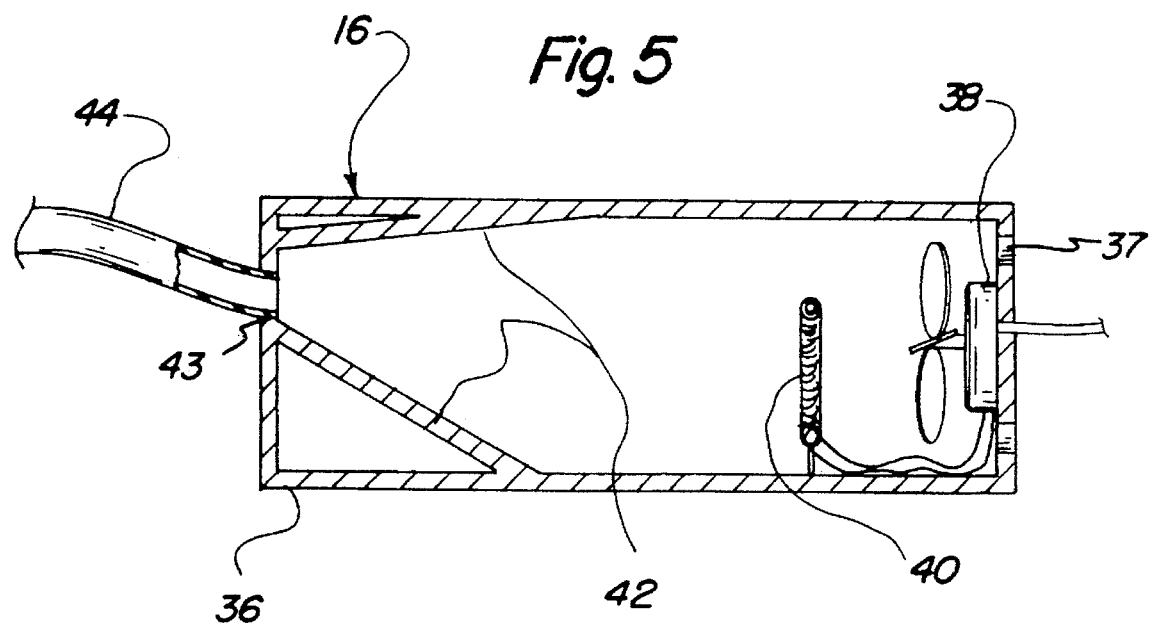
FIG. 5 is across sectional view taken along line 5—5 of FIG. 3.
Figure 6:
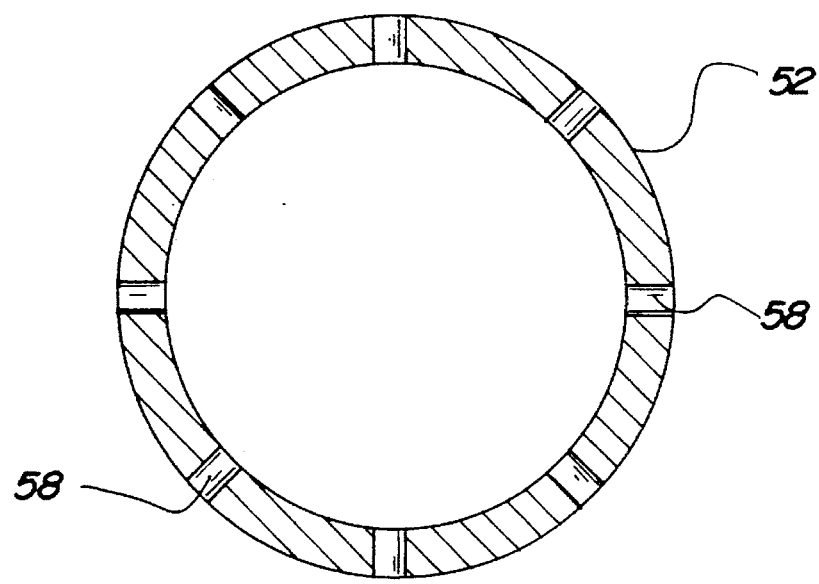
FIG. 6 is a cross sectional view taken along line 6—6 of FIG. 1.

Referring now to FIG. 5, it can be shown that the blower means 16 according to the present invention 10 preferably includes a blower housing 36 having a fan 38 mounted therewithin. The fan 38 is electrically powered and operates to draw in through apertures 37 in the blower housing 36 and force such air across a heating coil 40. A pair of guide plates 42 mounted within the blower housing 36 guide the heated air towards an exit aperture 43 through which a blower conduit 44 fluidly communicates with an interior of the blower housing 36. As shown in FIG. 3, the vapor conduit 28 orthogonally intersects the blower conduit 44 such that air passing through the blower conduit will draw vapor from the vapor generating means 14 and into the blower conduit through the venturi effect. The blower conduit 44 is subsequently positioned in fluid communication with the diffuser means 18 so as to dispense the heated and diluted vapor into the associated room.

Referring back now to FIGS. 1 through 3, it can be shown that the diffuser means 18 according to the present invention 10 preferably comprises a rectangular diffuser 46 including a first vertical conduit 48 spaced from and oriented parallel to a second vertical conduit 50, with an upper horizontal conduit 52 extending between upper distal ends of the vertical conduits. Similarly, and as shown only in FIG. 3, a lower horizontal conduit 54 extends between lower distal ends of the vertical conduits 48 and 50 to complete the rectangular shape of the diffuser 46. Also shown in FIG. 3 is a distribution manifold 56 which fluidly communicates the vertical conduits 48 and 50 with the blower conduit 44 to provide for an equal distribution of the heated and diluted vapor into both vertical conduits. Preferably, the rectangular diffuser 46 is received within a correspondingly shaped recess of the housing 12 substantially as shown. Referring now to FIG. 6, it can be shown that the conduits 48–54 of the rectangular diffuser 46 each include a plurality of dispensing apertures 58 extending therethrough. The dispensing apertures 58 are preferably equally radially spaced about the conduits 48–54 such that the vapor is distributed equally in all directions. By this structure, an operation of the device 10 within a room will result in an equal distribution of the vapor towards all walls of the structure. Further, medical instruments or other individual items to be disinfected can be placed on top of the housing 12 so as to receive a thorough coating of the heating vapor. Because the heating coil 40 heats the air entering the blower conduit 44, the vapor is dispensed at an elevated temperature relative to the ambient air within the room. Thus, subsequent evaporation of the germicidal fluid from the walls of the room and the associated equipment contained therein will occur at an expedited rate.

In use, the germicide diffuser 10 according to the present invention can be easily positioned within a room to be disinfected. The device 10 will then dispense a heated and diluted vapor mist of a germicide fluid onto the associated room and equipment to effect chemical disinfecting thereof. Preferably, the housing 12 includes rotatable wheels or casters which permit the device to be substantially portable in operation.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A germicide diffuser comprising:

a housing positionable within a room to be disinfected;

a vapor generating means mounted within the housing for mechanically atomizing a fluid germicide, the vapor generating means comprising a fluid reservoir within which a germicidal fluid is positionable, a motor mounted to a top end of the fluid reservoir, a centrifugal atomizer coupled to the motor and extending into the fluid reservoir, and a vapor conduit extending from an upper extent of the fluid reservoir to a remote location to thus permit exiting of atomized fluid germicide;

a blower means in fluid communication with the vapor generating means for diluting and heating a fluid vapor generated by the vapor generating means; and a diffuser means mounted to an exterior of the housing and fluidly communicating with the blower means for distributing diluted and heated vapor.

2. The germicide diffuser of claim 1, wherein the centrifugal atomizer comprises an elongated and tapered rotor coupled to the motor and extending into the fluid reservoir; a connecting web coupled to the tapered rotor and extending radially outwardly therefrom; and a cylindrical screen supported in a concentric orientation relative to the tapered rotor by the connecting web.

3. The germicide diffuser of claim 2, wherein the blower means includes a blower housing having a plurality of apertures extending therethrough and an exit aperture; a fan mounted within the blower housing for drawing air in through the apertures in the blower housing; a heating coil mounted within the blower housing; a blower conduit fluidly communicating with an interior of the blower housing through the exit aperture, the vapor conduit orthogonally intersecting the blower conduit such that air passing through the blower conduit will draw vapor from the vapor generating means into the blower conduit.

4. The germicide diffuser of claim 3, wherein the diffuser means comprises a rectangular diffuser including a first vertical conduit spaced from and oriented parallel to a second vertical conduit, with an upper horizontal conduit extending between upper distal ends of the vertical conduits, and a lower horizontal conduit extending between lower distal ends of the vertical conduits, the diffuser means further comprising a distribution manifold in fluid communication with the vertical conduits and with the blower conduit, wherein the conduits of the rectangular diffuser each include a plurality of dispensing apertures extending therethrough, the dispensing apertures being equally radially spaced about the conduits.

5. The germicide diffuser of claim 4, wherein the housing includes a top wall such that individual items to be disinfected can be placed on the top wall of the housing to receive a coating of heated vapor.

* * * * *